United States Patent [19]
Romano et al.

[11] Patent Number: 5,206,409
[45] Date of Patent: Apr. 27, 1993

[54] PROCESS FOR PREPARING DI-ALKYL CARBONATES

[75] Inventors: Ugo Romano, Vimercate; Franco Rivetti, Schio, both of Italy

[73] Assignee: Enichem Synthesis, S.p.A., Palermo, Italy

[21] Appl. No.: 734,014

[22] Filed: Jul. 19, 1991

Related U.S. Application Data

[63] Continuation of Ser. No. 420,542, Oct. 11, 1989, abandoned.

[30] Foreign Application Priority Data

Oct. 19, 1988 [IT] Italy ............................... 22353 A/88

[51] Int. Cl.$^5$ ............................................ C07C 69/96
[52] U.S. Cl. .................................................. 558/277
[58] Field of Search ........................................ 538/277

[56] References Cited

U.S. PATENT DOCUMENTS

| | | | |
|---|---|---|---|
| 4,360,477 | 11/1992 | Hallgren et al. | 558/277 |
| 4,761,467 | 8/1988 | Bhattacharya | 558/277 |
| 4,785,130 | 11/1988 | Bhattacharya | 558/277 |

Primary Examiner—José G. Dees
Assistant Examiner—Joseph M. Conrad, III
Attorney, Agent, or Firm—Hedman, Gibson & Costigan

[57] ABSTRACT

A process is described for preparing a di-alkyl carbonate, e.g. dimethylcarbonate, via oxidative carbonylation of the corresponding alkanol, e.g. methanol, in the presence of a catalyst system which comprises a copper alkoxy-halide and a quantity of between 0.5 and 10 mol % of $Cu X_2$ or HX with respect to the total moles of copper. In this manner extremely high di-alkyl carbonate formation rates are obtained.

3 Claims, 1 Drawing Sheet

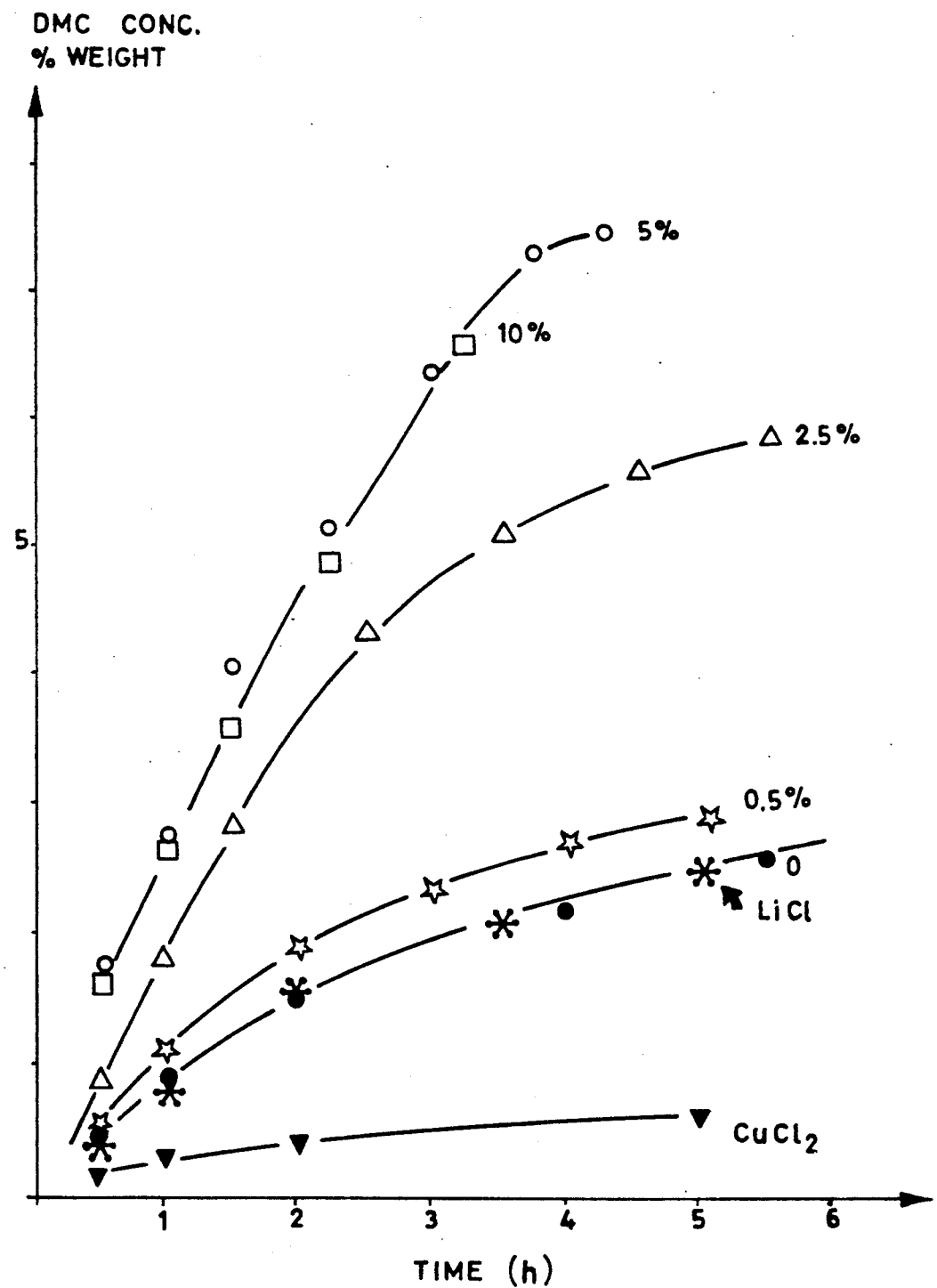

PROCESS FOR PREPARING DI-ALKYL CARBONATES

This application is a continuation of application Ser. No. 07/420,542 filed Oct. 11, 1989, now abandoned.

This invention relates to an improved process for preparing dialkyl carbonates. More particularly, the invention relates to an improved process for preparing dimethylcarbonate (DMC). DMC is an extremely versatile product which is used instead of phosgene in the synthesis of other alkyl and aryl carbonates, which are themselves used as synthetic lubricants, solvents, plasticisers, monomers for organic glasses etc., in methylation and carbonylation reactions, in the preparation of isocyanates, urethanes and polycarbonates, as a fuel additive, as an organic solvent etc.

DESCRIPTION OF THE PRIOR ART

The classical method of preparing DMC consists of reacting methyl alcohol with phosgene (see for example Kirk-Othmer, Encyclopedia of Chemical Technology, 3rd Ed., Vol. 4, p. 758). This method suffers from numerous technical problems due to the use of phosgene and to the co-production of hydrochloric acid (safety, corrosion, product specifications, need for a hydrochloric acid acceptor with consequent stoichiometric production of NaCl). To obviate these problems various alternative synthesis methods have been studied.

SUMMARY OF THE INVENTION

Among these, the oxidative carbonylation of methanol in the presence of suitable catalysts has aroused particular interest in recent years. In particular, it is known to use palladium compounds as catalysts (U.S. Pat. No. 4,361,519, DE-A-3,212,535 and GB-B-2,148,881), the use of which however has two serious drawbacks, namely the co-production of oxalic acid esters [see Fenson, J. Org. Chem., 39, 701 (1974)] and the negative effect of the water co-produced in the reaction, which makes the catalyst system ineffective even at very low concentration levels. It is also known to use copper compounds (U.S. Pat. No. 3,846,468, U.S. Pat. No. 4,218,391, U.S. Pat. No. 4,318,862, U.S. Pat. No. 4,360,477, U.S. Pat. No. 4,625,044, EP-A-71,286, EP-A-134,668, EP-A-217,651, DE-A-3,212,535 and DE-A-3,016,187) and in particular the use of copper alkoxy-halides of formula Cu(OR)X where R is an alkyl group and X is a halogen atom. These catalysts can in fact be used in dispersion, in the absence of organic ligands and/or co-solvents, with many process advantages such as increased simplicity, easier reaction product and catalyst separation, suppression of carbonate hydrolysis by the action of the water co-produced as the result of basic catalysis induced by the ligands (such as pyridine), lower sensitivity of the catalyst system to the co-products $H_2O$ and $CO_2$, etc.

In addition, this catalyst can be conveniently prepared by oxidising the cuprous halide CuX in the initial alkanol with oxygen or air, this forming the basis for the creation of a catalytic cycle in that the subsequent di-alkyl carbonate formation reaction involves the reduction of Cu(II) to Cu(I) in accordance with the following overall reaction scheme:

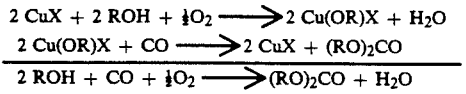

BRIEF DESCRIPTION OF THE FIGURE

FIG. 1 gives a graphical representation of the data that appears in the tables to follow, showing the increase in the concentration of DMC over time, when the instant process is used.

When operating in the presence of water, it is known that the cupric alkoxy-halide undergoes more or less extended hydrolysis phenomena, the catalyst system then consisting of mixtures of copper salts of various degrees of halogenation, containing halide and hydroxide anions, and characterised by an overall molar halogen/copper ratio of 1. These mixtures can also be formed synthetically starting from cupric halides and oxides, hydroxides or carbonates, the mixtures obtained in this manner having the same catalytic behaviour as the cupric alkoxy-halide in the same reaction system.

For the purposes of the present invention, the term "cupric alkoxy-halide" therefore means not only the compound itself but also those copper salt mixtures obtainable by hydrolysing the compound in an aqueous alkanol environment, by oxidising the cuprous halide in an aqueous alkanol environment, or by synthetic formation starting from copper halides and oxides, hydroxides or carbonates, and characterised by an overall molar halogen/copper ratio of 1.

It has now been surprisingly found that when a lower alkanol ROH is subjected to oxidative carbonylation in the presence of a copper alkoxy-halide, the addition of a small quantity of $CUX_2$ or HX enables a very much higher di-alkyl carbonate formation rate to be obtained without any negative effect on the selectivity of the reaction. More specifically, it has been found that on subjecting a lower alkanol ROH, where R is a lower alkyl such as methyl, ethyl, propyl or isopropyl and preferably methyl, to oxidative carbonylation in the presence of a catalyst system consisting of a copper alkoxy-halide of formula Cu(OR)X where R has the aforesaid meaning and X is a halogen atom, preferably a chlorine or bromine atom, and more preferably a chlorine atom, the addition of a quantity of $CuX_2$ or HX of between 0.5 and 10 mol % with respect to the total moles of copper present in the system (corresponding to an overall molar halogen/copper ratio of between 1.005 and 1.100) and preferably between 2.5 and 10% (corresponding to an overall molar halogen/copper ratio of between 1.025 and 1.100), results in a considerable increase in the rate of formation of the di-alkyl carbonate. In particular, for equal reaction conditions and reaction time, the addition of a quantity of $CuCl_2$ or HCl of the order of 2.5–10 mol % results in approximately double the conversion of the alkanol into the corresponding di-alkyl carbonates. This result is even more surprising when considering that it is known (U. Romano et al., Ind. Eng. Chem. Prod. Res. Dev., 1980, 19, 396–403) that the use of $CUCl_2$ as catalyst in the oxidative carbonylation of methanol results on the one hand in extremely low reaction rates and on the other hand in selectivity losses with the formation of by-products at the expense of the methanol.

It has also been verified that this positive effect is specific for $CuCl_2$ and HCl, in that the addition of chlorine ions in other form, such as LiCl, has no effect on the reaction rate. The same effect can also be achieved using synthetic mixtures of copper halides and oxides, hydroxides or carbonates, as indicated heretofore, where however the overall molar halogen/copper ratio is between 1.005 and 1.100.

The oxidative carbonylation reaction using the catalyst system of the present invention is conducted in accordance with the practice generally followed for oxidative carbonylation using copper catalysts. In particular, the quantity of copper present in the reaction mixture is not critical and any quantity able to produce the desired catalytic effect can be used. However, in general a quantity of between about 0.1 and about 50 parts, and preferably between about 1 and about 30 parts, of catalyst per 100 parts of feed alkanol have proved suitable.

As already seen, the process of the invention can be used to prepare di-alkyl carbonates, and in particular di-methyl, di-ethyl, di-propyl or di-isopropyl carbonates, although a preferred aspect of the present invention is its use in the preparation of DMC. The copper alkoxy-halide used in the catalyst system of the invention can therefore be a copper methoxy-, ethoxy-, propoxy- or isopropoxy-halide, and preferably a copper methoxy-halide. More preferably, said methoxy-halide is a copper methoxy-bromide or, even more preferably, a copper methoxy-chloride.

The reaction is implemented in practice by dissolving or dispersing the catalyst system in the reaction medium, consisting essentially of the alkanol possibly mixed with an inert solvent such as a hydrocarbon, a halogenated hydrocarbon, an ester or an ether, and passing through this system a stream of oxygen (which can also be in the form of air) and a stream of CO. These streams can be fed either together or separately, and in this latter case either simultaneously or in alternate cycles.

It is also possible to use gaseous mixtures containing such gases in mixture with others, such as $H_2$, $N_2$, $CO_2$ or $CH_4$, which behave as inert gases and do not give rise to secondary reactions in the reaction system. In particular, as described in U.S. Pat. No. 4,318,862, it can be convenient to use the carbon monoxide in mixture with hydrogen, e.g. in the form of synthesis gas.

The reaction is conveniently conducted at a temperature of between 50° and 200° C. and preferably between 70° and 150° C., and at a pressure of between atmospheric and 100 atmospheres and preferably between 10 and 100 atmospheres, in that the reaction rate increases with the carbon monoxide pressure.

On termination of the reaction the reaction products and the catalyst system can be easily separated from the system by physical means (e.g. distillation, filtration etc.) as known in this field.

The invention is further illustrated by the following examples.

EXAMPLES 1–4

$Cu(OCH_3)Cl$ and anhydrous $CuCl_2$ (a total of 1.68 moles/l, of which the $CuCl_2$ percentages are as shown in Table 1) plus methyl alcohol (100 ml) are introduced into a 250 ml pressure vessel lined with Teflon ®. The system is placed under carbon monoxide and reacted at 75° C. and 12 atg, the formation of DMC being monitored with time by gas chromatography. The results are given in Table 1 below.

TABLE 1

| Ex No. | mol %* $CuCl_2$ | DMC concentration (wt %) at t (min) | | | | | | | |
|---|---|---|---|---|---|---|---|---|---|
| | | 60 | 90 | 120 | 150 | 180 | 210 | 240 | 300 |
| 1 | 0.5 | 1.12 | — | 1.90 | — | 2.35 | — | 2.75 | 2.90 |
| 2 | 2.5 | 1.78 | 2.85 | — | 4.35 | — | 5.10 | — | — |
| 3 | 5.0 | 2.75 | 4.06 | — | — | 6.38 | — | — | — |
| 4 | 10.0 | 2.72 | 3.60 | — | — | 6.51** | — | — | — |

*with respect to the total moles of copper present
**value obtained at 195 minutes

EXAMPLES 5–7

The reaction is repeated under the same conditions but using in place of the $Cu(OCH_3)Cl/CuCl_2$ catalyst system only $Cu(OCH_3)Cl$ (1.68 mols/l) (Ex. 5), only $CuCl_2$ (1.68 moles/l) (Ex. 6) or a mixture of ($Cu(OCH_3)Cl$ (1.68 moles/l) and LiCl (10 mol %) (Ex. 7), with the results given in Table 2.

TABLE 2

| Ex No. | DMC concentration (wt %) at t (min) | | | | | |
|---|---|---|---|---|---|---|
| | 60 | 120 | 180 | 210 | 240 | 300 |
| 5 | 0.88 | 1.50 | — | — | 2.18 | — |
| 6 | 0.30 | 0.45 | — | — | — | 0.65 |
| 7 | 0.80 | 1.60 | — | 2.10 | — | 2.50 |

For a better interpretation of these results they are summarised graphically in Figure.

EXAMPLES 8–10

The rate of DMC formation is measured in the reduction of copper methoxychloride (1.68 moles/l) in methanol with carbon monoxide at 95° C. and 15 atg total pressure, after adding varying quantities of HCl. The observed reaction kinetics show that the reaction is of zero order with respect to the copper salts, thus the DMC formation rate is constant (moles/l.h). The results are shown in Table 3 below.

TABLE 3

| Ex No. | mol % HCl/Cu(OCH₃)Cl | $R_{DMC}$ (moles/l.h) |
|---|---|---|
| 8 | 0 | 0.2 |
| 9 | 5 | 0.52 |
| 10 | 10 | 0.58 |

We claim:

1. A process for increasing the rate of formation of di-alkyl carbonate via oxidative carbonylation of the corresponding lower alkanol in the presence of a catalyst system wherein said catalyst system consists essentially of a copper alkoxy halide and a quantity of between 0.5 and 10 mol % of $CuX_2$ with respect to the total moles of copper, where X is a halogen atom; and wherein the overall halogen to copper molar ratio ranges from 1.005 to 1.100.

2. A process as defined in claim 1, wherein said lower alkanol is methanol, said X is chlorine; and wherein said reaction is effected at a temperature of between 50° and 200° C. an at a pressure of between 1 and 100 atmospheres.

3. A process as defined in claim 2 wherein the catalyst system contains a $CuX_2$ quantity of between 2.5 and 10 mol % with respect to the total moles of copper; and wherein the overall halogen to copper molar ratio ranges from 1.025 to 1.100.

* * * * *